(12) United States Patent
Pratt et al.

(10) Patent No.: US 6,962,610 B2
(45) Date of Patent: Nov. 8, 2005

(54) HAIR DYE COMPOSITION

(75) Inventors: Dominic Pratt, Darmstadt (DE); Toshio Kawagishi, Minamiashigara (JP)

(73) Assignees: Kao Corporation, Tokyo (JP); Fuji Photo Film Co., Ltd., Minamiashigara (JP)

( * ) Notice: Subject to any disclaimer, the term of this patent is extended or adjusted under 35 U.S.C. 154(b) by 11 days.

(21) Appl. No.: 10/660,536

(22) Filed: Sep. 12, 2003

(65) Prior Publication Data

US 2004/0117922 A1 Jun. 24, 2004

(30) Foreign Application Priority Data

Sep. 13, 2002 (JP) ........................................ 2002-269173

(51) Int. Cl.$^7$ ............................................... A61K 7/13
(52) U.S. Cl. ...................... 8/405; 8/662; 8/677; 8/678; 8/690; 8/691; 8/692
(58) Field of Search ............................ 8/405, 662, 677, 8/678, 690, 691, 692

(56) References Cited

U.S. PATENT DOCUMENTS

| | | | |
|---|---|---|---|
| 5,124,354 A | * | 6/1992 | Green ........................ 514/520 |
| 6,451,069 B2 | | 9/2002 | Matsunaga et al. ............ 8/405 |
| 2002/0010969 A1 | * | 1/2002 | Goettel et al. ................. 8/405 |

FOREIGN PATENT DOCUMENTS

| | | |
|---|---|---|
| DE | 198 42 070 | 3/2000 |
| DE | 199 51 134 | 4/2001 |
| EP | 0 474 191 | 3/1992 |
| JP | 6-48050 | 2/1994 |
| JP | 6-271435 | 9/1994 |

\* cited by examiner

Primary Examiner—Eisa Elhilo
(74) Attorney, Agent, or Firm—Oblon, Spivak, McClelland, Maier & Neustadt, P.C.

(57) ABSTRACT

Provided is a hair dye composition containing a dissociative direct dye represented by the following formula (1):

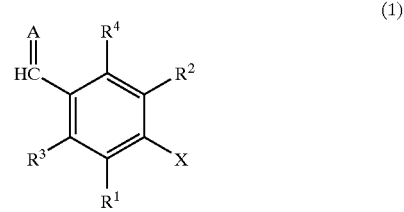

(1)

wherein, $R^1$ to $R^4$ each represents H or substituent, X represents OH or $-NHSO_2R^5$, $R^5$ represents an alkyl, aryl or heterocyclic group, and A represents a divalent group capable of forming a methine dye as a whole compound, together with the portion other than A.

The hair dye composition of the present invention is capable of strongly dyeing the hair with a vivid color tone without causing decomposition of the dye during the dyeing process, exhibits an excellent resistance against sunlight, hair washing, perspiration, friction and heat, has a high stability against an alkali agent and an oxidizing agent, has a high dyeing property, and has less color fade after the passage of time.

12 Claims, No Drawings

HAIR DYE COMPOSITION

BACKGROUND OF THE INVENTION

1. Field of the Invention

The present invention relates to a hair dye composition having excellent dyeing power, being capable of imparting a wide range of colors to the hair without losing their vividness, and having less color fade over time.

2. Background Art

Hair dyes can be classified by a dye to be used therefor, or by whether they have bleaching action of melanin or not. Typical examples include a two-part permanent hair dye composed of a first part containing an alkali agent, an oxidation dye and optionally a direct dye such as a nitro dye and a second part containing an oxidizing agent; and a one-part semi-permanent hair dye containing an organic acid or an alkali agent, and an acid dye, basic dye or direct dye such as a nitro dye.

The above-described permanent hair dye is however accompanied by the drawback that the color tone imparted by an oxidation dye is not so vivid. Use of a nitro dye or cationic dye for a two-component hair dye containing an oxidizing agent has been attempted in order to produce various color tones (refer to, for example, Japanese Patent Laid-Open Nos. 271435/1994 and 2001-261535). A hair dye added with a nitro dye develops a vivid color just after dyeing, but color fades away remarkably with elapse of the time and tends to be dull. Use of a cationic dye, on the other hand, involves such problems that it is easily decomposed when mixed with a peroxide serving as an oxidizing agent and it cannot readily be used in combination with an anionic polymer.

SUMMARY OF THE INVENTION

An object of the present invention is to provide a hair dye composition comprising a dissociative direct dye represented by the following formula (1):

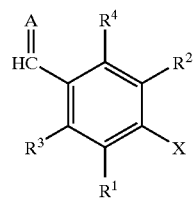

(1)

wherein, $R^1$, $R^2$, $R^3$ and $R^4$ each independently represents a hydrogen atom or a substituent, and X represents a hydroxyl group or —$NHSO_2R^5$, in which $R^5$ represents an alkyl, aryl or heterocyclic group, with the proviso that each of the above-described groups may further have one or more substituents; and A represents a divalent group capable of forming a methine dye as a whole compound together with the portion other than A.

DETAILED DESCRIPTION OF THE INVENTION

The present invention relates to a hair dye composition capable of dyeing the hair strongly into a vivid color tone without causing decomposition of the dye during the dyeing process, and exhibiting an excellent resistance against sunlight, hair washing, perspiration, friction and heat, having a high stability against an alkali agent and an oxidizing agent, having high dyeing properties, and having less color fade even after passage of time; and a hair dyeing method using the composition.

The dissociative direct dye of formula (1) used in the present invention has a phenolic hydroxyl group or a sulfonamide group —$NHSO_2R^5$. At a certain pH or greater, proton dissociation occurs in the dye, which causes a change in color hue, thereby imparting a desired color hue to the hair. The dissociative direct dye (1) preferably does not contain, in the molecule thereof, a group which dissociates at a neutral pH, such as carboxyl group, sulfo group or quaternary ammonium group.

In formula (1), examples of the substituent represented by $R^1$, $R^2$, $R^3$, or $R^4$ include halogen atoms, alkyl groups, alkenyl groups, alkynyl groups, aryl groups, heterocyclic groups, a cyano group, a hydroxy group, a nitro group, a carboxyl group, alkoxy groups, aryloxy groups, silyloxy groups, heterocyclic oxy groups, acyloxy groups, carbamoyloxy groups, alkoxycarbonyloxy groups, aryloxycarbonyloxy groups, amino group, alkylamino groups, arylamino groups, heterocyclic amino groups, acylamino groups, ureido groups, alkoxycarbonylamino groups, aryloxycarbonylamino groups, sulfamoylamino groups, alkylsulfonylamino groups, arylsulfonylamino groups, mercapto group, alkylthio groups, arylthio groups, heterocyclic thio groups, sulfamoyl groups, sulfo group, alkylsulfinyl groups, arylsulfinyl groups, alkylsulfonyl groups, arylsulfonyl groups, acyl groups, alkoxycarbonyl groups, aryloxycarbonyl groups, carbamoyl groups, arylazo groups, heterocyclic azo groups, phosphino groups, phosphinyl groups, phosphinyloxy groups, phosphinylamino groups and silyl groups. When these substituents are further substitutable, they may have one or more substituents.

Specific examples of the above-described substituents (including the case where they are substituted further) will next be described.

The halogen atoms include fluorine, chlorine, bromine and iodine atoms.

The alkyl groups include linear, branched or cyclic $C_{1-10}$, preferably $C_{1-6}$ alkyl groups such as methyl, ethyl, n-propyl, isopropyl, t-butyl, n-octyl, 2-chloroethyl, 2-cyanoethyl, 2-ethylhexyl, cyclopropyl and cyclopentyl.

The alkenyl groups include linear, branched or cyclic $C_{2-10}$, preferably $C_{2-6}$ alkenyl groups such as vinyl, allyl, prenyl and cyclopenten-1-yl.

The alkynyl groups include $C_{2-10}$, preferably $C_{2-6}$ alkynyl groups such as ethynyl and propargyl.

The aryl groups include $C_{6-12}$, preferably $C_{6-8}$ aryl groups such as phenyl, p-tolyl, naphthyl, 3-chlorophenyl and 2-aminophenyl.

The heterocyclic groups include aromatic or nonaromatic, monovalent $C_{1-12}$, preferably $C_{2-6}$ groups obtained by removing one hydrogen atom from a 5- or 6-membered heterocyclic compound, such as 1-pyrazolyl, 1-imidazolyl, 2-furyl, 2-thienyl, 2-thiazolyl, benzothiazol-2-yl, isothiazol-5-yl, benzoisothiazol-7-yl, oxazol-2-yl, benzoxazol-2-yl, 1,2,4-thiadiazol-5-yl, 1,3,4-thiadiazol-2-yl, 1,2,4-oxadiazol-5-yl, 1,3,4-oxadiazol-2-yl, 1,2,4-triazol-3-yl, 4-pyridyl, 3-pyridyl, 4-pyrimidinyl and qunazolin-4-yl.

The alkoxy groups include linear, branched or cyclic, $C_{1-10}$, preferably $C_{1-6}$ alkoxy groups such as methoxy, ethoxy, isopropoxy, t-butoxy, cyclopentyloxy, 2-buten-1-yloxy and 2-methoxyethoxy.

The aryloxy groups include $C_{6-12}$, preferably $C_{6-8}$ aryloxy groups such as phenoxy, 2-methylphenoxy, 4-t-butylphenoxy and 3-nitrophenoxy.

The silyloxy groups include $C_{3-10}$, preferably $C_{3-6}$ silyloxy groups such as trimethylsilyloxy and t-butyldimethylsilyloxy.

The heterocyclic oxy groups include $C_{1-12}$, preferably $C_{2-6}$ heterocyclic oxy groups such as 1-phenyltetrazol-5-oxy and 2-tetrahydropyranyloxy.

The acyloxy groups include $C_{1-12}$, preferably $C_{1-8}$ acyloxy groups such as formyloxy, acetyloxy, pivaloyloxy, benzoyloxy and p-methoxyphenylcarbonyloxy.

The carbamoyloxy groups include $C_{1-10}$, preferably $C_{1-6}$ carbamoyloxy groups such as N,N-dimethylcarbamoyloxy, N,N-diethylcarbamoyloxy, morpholinocarbonyloxy, and N-n-octylcarbamoyloxy.

The alkoxycarbonyloxy groups include $C_{2-10}$, preferably $C_{2-6}$ alkoxycarbonyloxy groups such as methoxycarbonyloxy, ethoxycarbonyloxy, t-butoxycarbonyloxy and n-octyloxycarbonyloxy.

The aryloxycarbonyloxy groups include $C_{7-12}$, preferably $C_{7-10}$ aryloxycarbonyloxy groups such as phenoxycarbonyloxy and p-methoxyphenoxycarbonyloxy.

The alkylamino groups include $C_{1-10}$, preferably $C_{1-6}$ alkylamino groups such as methylamino and dimethylamino.

The arylamino groups include $C_{6-12}$, preferably $C_{6-8}$ arylamino groups such as anilino, N-methylanilino and diphenylamino.

The heterocyclic amino groups include $C_{1-12}$, preferably $C_{2-6}$ heterocyclic amino groups such as imidazol-2-ylamino and pyrazol-3-ylamino.

The acylamino groups include $C_{1-10}$, preferably $C_{1-6}$ alkylcarbonylamino groups such as formylamino, acetylamino and pivaloylamino, $C_{6-12}$, preferably $C_{6-8}$ arylcarbonylamino groups such as benzoylamino, $C_{2-12}$, preferably $C_{2-6}$ heterocyclic carbonylamino groups such as pyridine-4-carbonylamino, thiophene-2-carbonylamino and morpholinocarbonylamino, and $C_{2-10}$, preferably $C_{4-8}$ imido groups such as N-succinimido and N-phthalimido.

The ureido groups include $C_{1-12}$, preferably $C_{1-6}$ ureido groups such as carbamoylamino, N,N-dimethylureido and N,N-diethylureido.

The alkoxycarbonylamino groups include $C_{2-10}$, preferably $C_{2-6}$ alkoxycarbonylamino groups such as methoxycarbonylamino, ethoxycarbonylamino and t-butoxycarbonylamino.

The aryloxycarbonylamino groups include $C_{7-12}$, preferably $C_{7-9}$ aryloxycarbonylamino groups such as phenoxycarbonylamino, p-chlorophenoxycarbonylamino and 4-methoxyphenoxycarbonylamino.

The sulfamoylamino groups include $C_{0-10}$, preferably $C_{0-6}$ sulfamoylamino groups such as sulfamoylamino, N,N-dimethylaminosulfonylamino and N-(2-hydroxyethyl)sulfamoylamino.

The alkylsulfonylamino groups include $C_{1-10}$, preferably $C_{1-6}$ alkylsulfonylamino groups such as methylsulfonylamino and butylsulfonylamino.

The arylsulfonylamino groups include $C_{6-12}$, preferably $C_{6-8}$ arylsulfonylamino groups such as phenylsulfonylamino, 2,3,5-trichlorophenylsulfonylamino and p-methylphenylsulfonylamino.

The alkylthio groups include $C_{1-10}$, preferably $C_{1-6}$ alkylthio groups such as methylthio, ethylthio and butylthio.

The arylthio groups include $C_{6-12}$, preferably $C_{6-8}$ arylthio groups such as phenylthio, p-chlorophenylthio and m-methoxyphenylthio.

The heterocyclic thio groups include $C_{2-10}$, preferably $C_{2-6}$ heterocyclic thio groups such as 2-benzothiazolylthio and 1-phenyltetrazol-5-ylthio.

The sulfamoyl groups include $C_{0-10}$, preferably $C_{0-6}$ sulfamoyl groups such as sulfamoyl, N-ethylsulfamoyl, N,N-dimethylsulfamoyl, N-acetylsulfamoyl and N-benzoylsulfamoyl.

The alkylsulfinyl groups include $C_{1-10}$, preferably $C_{1-6}$ alkylsulfinyl groups such as methylsulfinyl and ethylsulfinyl.

The arylsulfinyl groups include $C_{6-12}$, preferably $C_{6-8}$ arylsulfinyl groups such as phenylsulfinyl and p-methylphenylsulfinyl.

The alkylsulfonyl groups include $C_{1-10}$, preferably $C_{1-6}$ alkylsulfonyl groups such as methylsulfonyl and ethylsulfonyl.

The arylsulfonyl groups include $C_{6-12}$, preferably $C_{6-8}$ arylsulfonyl groups such as phenylsulfonyl and p-chlorophenylsulfonyl.

The acyl groups include formyl group, $C_{2-10}$, preferably $C_{2-6}$ alkylcarbonyl groups such as acetyl, pivaloyl and 2-chloroacetyl, and $C_{7-12}$, preferably $C_{7-9}$ arylcarbonyl groups such as benzoyl and 2,4-dichlorobenzoyl.

The alkoxycarbonyl groups include $C_{2-10}$, preferably $C_{2-6}$ alkoxycarbonyl groups such as methoxycarbonyl, ethoxycarbonyl, t-butoxycarbonyl and isobutoxycarbonyl.

The aryloxycarbonyl groups include $C_{7-12}$, preferably $C_{7-9}$ aryloxycarbonyl groups such as phenoxycarbonyl, 2-chlorophenoxycarbonyl, 3-nitrophenoxycarbonyl and 4-t-butylphenoxycarbonyl.

The carbamoyl groups include $C_{1-10}$, preferably $C_{1-6}$ carbamoyl groups such as carbamoyl, N-methylcarbamoyl, N,N-dimethylcarbamoyl, N-(2-hydroxyethyl)carbamoyl and N-(methylsulfonyl)carbamoyl.

The arylazo groups include $C_{6-12}$, preferably $C_{6-8}$ arylazo groups such as phenylazo and p-chlorophenylazo.

The heterocyclic azo groups include $C_{1-10}$, preferably $C_{1-6}$ heterocyclic azo groups such as pyrazol-3-ylazo, thiazol-2-ylazo, 5-ethylthio-1,3,4-thiadiazol-2-ylazo.

The phosphino groups include $C_{2-12}$, preferably $C_{2-6}$ phosphino groups such as dimethylphosphino, diphenylphosphino and methylphenoxyphosphino).

The phosphinyl groups include $C_{2-12}$, preferably $C_{2-6}$ phosphinyl groups such as phosphinyl and diethoxyphosphinyl.

The phosphinyloxy groups include $C_{2-12}$, preferably $C_{2-6}$ phosphinyloxy groups such as diphenoxyphosphinyloxy and dibutoxyphosphinyloxy.

The phosphinylamino groups include $C_{2-12}$, preferably $C_{2-6}$ phosphinylamino groups such as dimethoxyphosphinylamino and dimethylaminophosphinylamino.

The silyl groups include $C_{3-12}$, preferably $C_{3-8}$ silyl groups such as trimethylsilyl, t-butyldimethylsilyl and phenyldimethylsilyl.

When the above-described substituents $R^1$, $R^2$, $R^3$ and $R^4$ are groups which can be further substituted, they may have one or more substituents. In such a case, preferable substituents are those substituent groups as described above and a preferable range of the total number of the carbon atoms of $R^1$, $R^2$, $R^3$ and $R^4$ does not exceed the above-described range. When they have two or more substituents, the substituents may be the same or different.

In $—NHSO_2R^5$ represented by X in formula (1), the preferable number of carbon atoms of the alkyl group, aryl group or heterocyclic group represented by $R^5$ and specific examples of the group are the same as those described above for the substituents represented by $R^1$ to $R^4$.

The group represented by A in the formula (1) will next be described specifically. Compounds known as a coupler in the field of silver halide color photosensitive materials are preferred as A and a skeletal portion of couplers for silver halide color photography (a portion which will become a chromophore of a dye, by coupling with an oxidized aromatic amine developing agent) as described in detail in Research Disclosure 37038, February 1995, pages 80 to 85 and 87 to 89 are usable.

Preferred examples of the skeleton of an image-forming coupler known in the field of silver halide color photosensitive materials include pivaloylacetamide couplers, benzoylacetamide couplers, malonic diester couplers, malonic diamide couplers, dibenzoylmethane couplers, benzothiazolylacetamide couplers, malonic ester monoamide couplers, benzoxazolylacetamide couplers, benzimidazolylacetamide couplers, cyanoacetamide couplers, cycloalkylcarbonylacetamide couplers, indolin-2-yl-acetamide couplers, quinazolin-4-on-2-ylacetamide couplers as described in U.S. Pat. No. 5,021,332, benzo-1,2,4-thiadiazine-1,1-dioxid-3-yl-acetamide couplers as described in U.S. Pat. No. 5,021,330, couplers as described in European Patent No. 0421221, couplers as described in U.S. Pat. No. 5,455,149, couplers as described in European Patent Publication No. 0622673, and 3-indoloylacetamide couplers as described in European Patent Publication Nos. 0953871, 0953872 and 0953873.

Preferred examples of the skeleton of a magenta image-forming coupler include 5-pyrazolone couplers, 1H-pyrazolo[1,5-a]benzimidazole couplers, 1H-pyrazolo[5,1-c][1,2,4]triazole couplers, 1H-pyrazolo[1,5-b][1,2,4]triazole couplers, 1H-imidazo[1,2-b]pyrazole couplers, cyanoacetophenone couplers, active propene couplers as described in WO 93/01523, enamine couplers as described in WO 93/07534, 1H-imidazo[1,2-b][1,2,4]triazole couplers, and couplers as described in U.S. Pat. No. 4,871,652.

Preferred examples of the skeleton of a cyan image-forming coupler include phenol couplers, naphthol couplers, 2,5-diphenylimidazole couplers as described in European Patent Publication No. 0249453, 1H-pyrrolo[1,2-b][1,2,4]triazole couplers, 1H-pyrrolo[2,1-c][1,2,4]triazole couplers, pyrrole couplers as described in Japanese Patent Laid-Open Nos. 188137/1992 and 190347/1992, 3-hydroxypyridine couplers as described in Japanese Patent Laid-Open No. 315736/1989, pyrrolopyrazole couplers as described in U.S. Pat. No. 5,164,289, pyrroloimidazole couplers as described in Japanese Patent Laid-Open No. 174429/1992, pyrazolopyrimidine couplers as described in U.S. Pat. No. 4,950,585, pyrrolotriazine couplers as described in Japanese Patent Laid-Open No. 204730/1992; couplers as described in U.S. Pat. No. 4,746,602, couplers as described in U.S. Pat. No. 5,104,783, couplers as described in U.S. Pat. No. 5,162,196, and couplers as described in European Patent No. 0556700.

As the group represented by A in formula (1), preferred are groups represented by any one of the following formulas (Cp-1) through (Cp-11):

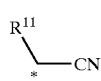
(Cp-1)

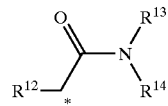
(Cp-2)

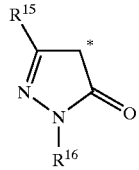
(Cp-3)

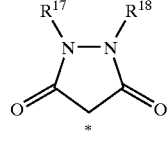
(Cp-4)

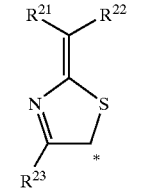
(Cp-5)

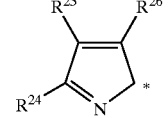
(Cp-6)

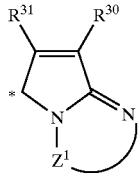
(Cp-7)

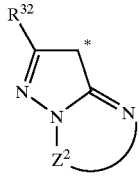
(Cp-8)

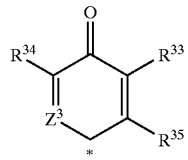
(Cp-9)

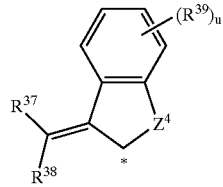
(Cp-10)

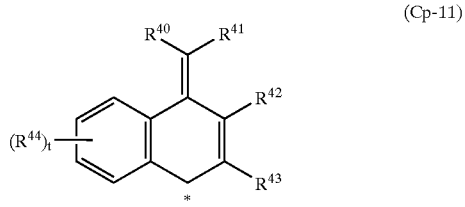

(in formulas (Cp-1) through (Cp-11), * is a position bonding to the benzylidene group in formula (1), in formula (Cp-1), $R^{11}$ represents a cyano group, acyl group, aryl group, heterocyclic group or group —$C(R^{101})$=$C(R^{102})$—$R^{103}$, in which $R^{101}$, $R^{102}$ and $R^{103}$ each independently represents a hydrogen atom or a substituent with the proviso that at least one of $R^{102}$ and $R^{103}$ is an electron attractive group having a Hammett σp value of 0.1 or greater, in formula (Cp-2), $R^{12}$ represents a cyano, acyl, alkoxycarbonyl, carbamoyl, aryl or heterocyclic group, and $R^{13}$ and $R^{14}$ each independently represents a hydrogen atom or an alkyl, aryl or heterocyclic group, in formula (Cp-3), $R^{15}$ represents a hydrogen atom or an alkyl, aryl, heterocyclic, amino, alkylamino, arylamino, heterocyclic amino, alkoxy, acylamino, alkoxycarbonylamino, ureido, alkoxycarbonyl, carbamoyl or cyano group, and $R^{16}$ represents a hydrogen atom or an alkyl, aryl or heterocyclic group, in formula (Cp-4), $R^{17}$ and $R^{18}$ each independently represents a hydrogen atom or an alkyl, aryl or heterocyclic group, in formula (Cp-5), $R^{21}$ and $R^{22}$ each independently represents a cyano, carbamoyl, alkoxycarbonyl, alkylsulfonyl or arylsulfonyl group, and $R^{23}$ represents a hydrogen atom or an alkyl, aryl or heterocyclic group, in formula (Cp-6), $R^{24}$, $R^{25}$ and $R^{26}$ each independently represents a hydrogen atom or a substituent, in formula (Cp-7), $R^{30}$ and $R^{31}$ each independently represents a hydrogen atom or a substituent, and $Z^1$ represents an atomic group necessary for the formation of a 5- or 6-membered ring together with N—C=N, in formula (Cp-8), $R^{32}$ represents a hydrogen atom or a substituent, and $Z^2$ represents an atomic group necessary for the formation of a 5- or 6-membered ring together with N—C=N, in formula (Cp-9), $R^{33}$, $R^{34}$ and $R^{35}$ each independently represents a hydrogen atom or a substituent, $Z^3$ represents a nitrogen atom or —$C(R^{36})$=, $R^{36}$ representing a hydrogen atom or a substituent, with the proviso that when $Z^3$ represents —$C(R^{36})$=, $R^{34}$ and $R^{36}$ may be coupled to form a 5-membered or 6-membered ring, in formula (Cp-10), $R^{37}$ and $R^{38}$ each independently represents a cyano, carbamoyl, alkoxycarbonyl, alkylsulfonyl or arylsulfonyl group, $R^{39}$ represents a hydrogen atom or a substituent, u stands for an integer of from 0 to 4, and $Z^4$ represents —$SO_2$— or —SO—, and in formula (Cp-11), $R^{40}$ and $R^{41}$ each independently represents a cyano, carbamoyl, alkoxycarbonyl, alkylsulfonyl or arylsulfonyl group, $R^{42}$, $R^{43}$ and $R^{44}$ each independently represents a hydrogen atom or a substituent, and t stands for an integer of from 0 to 4, with the proviso that the above-described groups may have one or more substituents.)

In the group represented by A, that is, a group represented by any one of formulas (Cp-1) through (Cp-11) in formula (1), the preferable number of carbon atoms of the group represented by $R^{11}$ to $R^{44}$ and $R^{101}$ to $R^{103}$ and specific examples of the group are similar to those described above in the substituents represented by $R^1$ to $R^4$, with the proviso that at least one of $R^{102}$ and $R^{103}$ is preferably an electron attractive group having a Hammett $\sigma_p$ value of 0.1 or greater, especially preferably 0.2 or greater. Examples of the electron attractive group having a Hammett $\sigma_p$ value of 0.1 or greater include a chlorine, bromine or iodine atom, or an alkoxycarbonyl, carbamoyl, alkylaminocarbonyl, dialkylaminocarbonyl, sulfamoyl, alkylaminosulfonyl, dialkylaminosulfonyl or acyl group. The Hammett empirical rule was advocated by L. P. Hammett in 1935 in order to quantitatively discuss the influence of a substituent on the reaction or equilibrium of a benzene derivative and its validity is now recognized widely. The substituent constants determined by the Hammett rule are $\sigma_p$ and $\sigma_m$ values. These values are found generally in many books and described in detail, for example, in *Lange's Handbook of Chemistry*, 12 ed., 1979, ed. J. A. Dean, published by McGraw-Hill, *Journal of Japanese Chemistry*, Extra Number, 122, 96–103 (1979) published by Nankodo, and *Chemical Review*, 91, 165–195(1991).

A preferable range of the dissociative direct dye (1) will next be described.

As $R^1$ or $R^2$ in formula (1), preferred are a hydrogen atom, halogen atoms, alkyl groups, a cyano group, acylamino groups, ureido groups, alkoxycarbonylamino groups, aryloxycarbonylamino groups, sulfamoylamino groups, alkylsulfonylamino groups, arylsulfonylamino groups, alkoxycarbonyl groups, sulfamoyl groups and carbamoyl groups, of which a hydrogen atom, chlorine atom, bromine atom, alkyl groups, acylamino groups, ureido groups, alkoxycarbonylamino groups, alkylsulfonylamino groups, arylsulfonylamino groups and carbamoyl groups are more preferred, with a hydrogen and chlorine atoms and acylamino and carbamoyl groups being most preferred.

As $R^3$ or $R^4$ in formula (1), preferred are a hydrogen atom, halogen atoms, alkyl groups and acylamino groups, of which a hydrogen atom, chlorine atom and alkyl groups are more preferred, with a hydrogen atom being most preferred.

As X in formula (1), a hydroxyl group is more preferred. When X represents —$NHSO_2R^5$, $R^5$ preferably represents an alkyl group.

As A in formula (1), the below-described groups are preferred.

In formula (Cp-1), preferred as $R^1$ are a cyano group, acyl groups, heterocyclic groups and —$C(R^{101})$=$C(R^{102})$—$R^{103}$, with the following groups being particularly preferred.

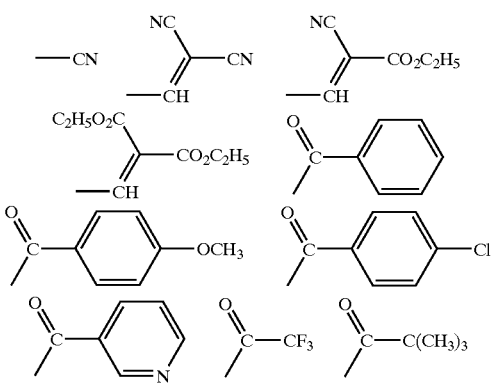

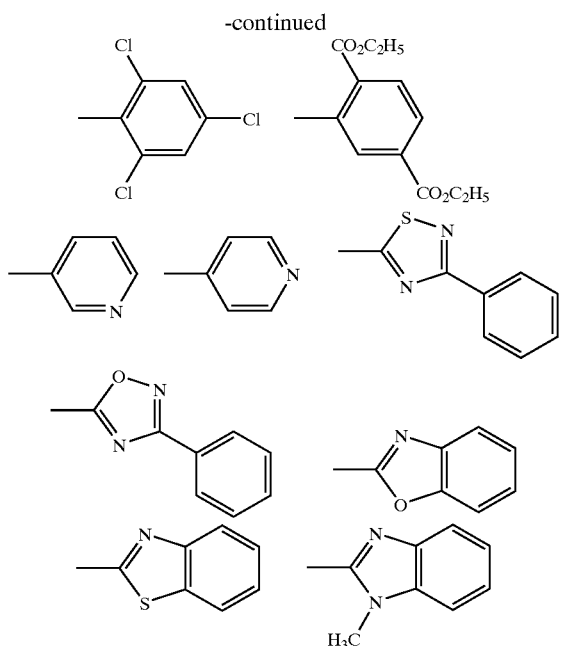

In formula (Cp-2), preferred as $R^{12}$ are a cyano group, acyl groups, aryl groups and heterocyclic groups. The cyano group, acyl groups and heterocyclic groups exemplified above as particularly preferred specific examples of $R^{11}$ are also preferred as $R^{12}$. As $R^{13}$ and $R^{14}$, a hydrogen atom, alkyl groups and aryl groups are preferred. It is preferred that at least one of $R^{13}$ and $R^{14}$ represents a hydrogen atom.

In formula (Cp-3), preferred as $R^{15}$ are alkyl groups, amino group, alkylamino groups, arylamino groups, heterocyclic amino groups, alkoxy groups, acylamino groups, alkoxycarbonylamino groups, ureido group, alkoxycarbonyl groups, carbamoyl groups and a cyano group, of which alkyl groups, acylamino groups, alkoxycarbonyl groups, carbamoyl groups and a cyano group are more preferred. As $R^{16}$, aryl groups and heterocyclic groups are preferred, with aryl groups being most preferred.

In formula (Cp-4), preferred as $R^{17}$ and $R^{18}$ are alkyl groups and aryl groups.

In formula (Cp-5), preferred as $R^{21}$ and $R^{22}$ are a cyano group, carbamoyl groups and alkoxycarbonyl groups, of which a cyano group and alkoxycarbonyl groups are more preferred. As $R^{23}$, a hydrogen atom, alkyl groups and aryl groups are preferred.

In formula (Cp-6), preferred as $R^{24}$ are a hydrogen atom, aryl groups, acylamino groups, alkylsulfonylamino groups and arylsulfonylamino groups. As $R^{25}$ and $R^{26}$, a hydrogen atom, aryl groups, alkoxycarbonyl groups, carbamoyl groups, alkylsulfonyl groups, arylsulfonyl groups and a cyano group are preferred, with aryl groups, alkoxycarbonyl groups, carbamoyl groups and a cyano group being more preferred.

In formula (Cp-7), preferred as $R^{30}$ and $R^{31}$ are a hydrogen atom, alkyl groups, aryl groups, heterocyclic groups, alkoxycarbonyl groups, carbamoyl groups, alkylsulfonyl groups, arylsulfonyl groups and a cyano group, of which alkyl groups, aryl groups, alkoxycarbonyl groups, carbamoyl groups and a cyano group are more preferred. As $Z^1$, groups capable of forming the following ring systems are preferred:

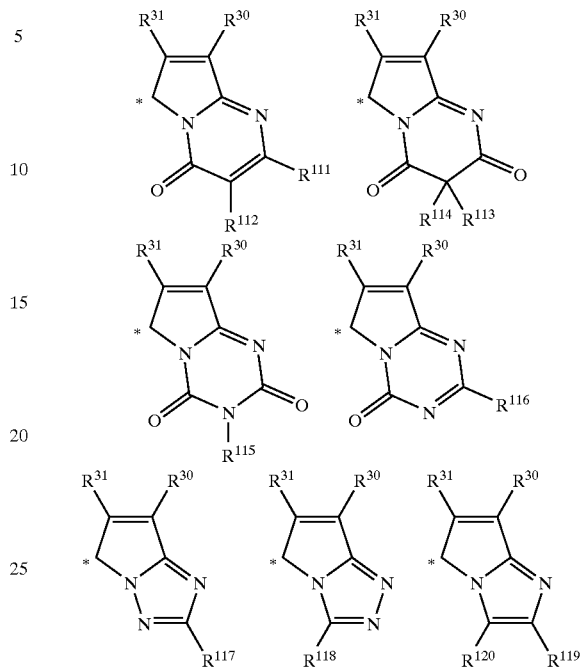

wherein, $R^{111}$ represents a hydrogen atom or an alkoxy, amino, alkylamino, arylamino, heterocyclic amino, acylamino, ureido, alkoxycarbonylamino, aryloxycarbonylamino, sulfamoylamino, alkylsulfonylamino, arylsulfonylamino, alkylthio, arylthio or heterocyclic thio group, $R^{112}$ represents a hydrogen or halogen atom, or an alkyl, acyl, carbamoyl or alkoxycarbonyl group, $R^{113}$ and $R^{114}$ each independently represents a hydrogen atom or an alkyl group, $R^{115}$ represents a hydrogen atom or an alkyl group, and $R^{116}$ represents a hydrogen atom or an alkyl, aryl, alkoxy, aryloxy, amino, alkylamino, arylamino, heterocyclic amino, acylamino, ureido, alkoxycarbonylamino, alkylsulfonylamino, arylsulfonylamino, alkylthio or arylthio group, $R^{117}$ and $R^{118}$ each independently represents a hydrogen atom or an alkyl, aryl or heterocyclic group, and $R^{119}$ and $R^{120}$ each independently represents a hydrogen atom or an alkyl, aryl, heterocyclic, acyl, alkoxycarbonyl or carbamoyl group or they may be coupled together to form a benzene ring.

The preferable number of the carbon atoms of $R^{111}$ to $R^{120}$ and specific examples thereof are similar to those described above in the substituents represented by $R^1$ to $R^4$.

In formula (Cp-8), preferred as $R^{32}$ are a hydrogen atom, alkyl groups, aryl groups, heterocyclic groups, alkoxycarbonyl groups, carbamoyl groups, alkylsulfonyl groups, arylsulfonyl groups and a cyano group, of which alkyl groups, aryl groups, alkoxycarbonyl groups, carbamoyl groups and a cyano group are more preferred. As $Z^2$, groups capable of forming the following ring systems are preferred.

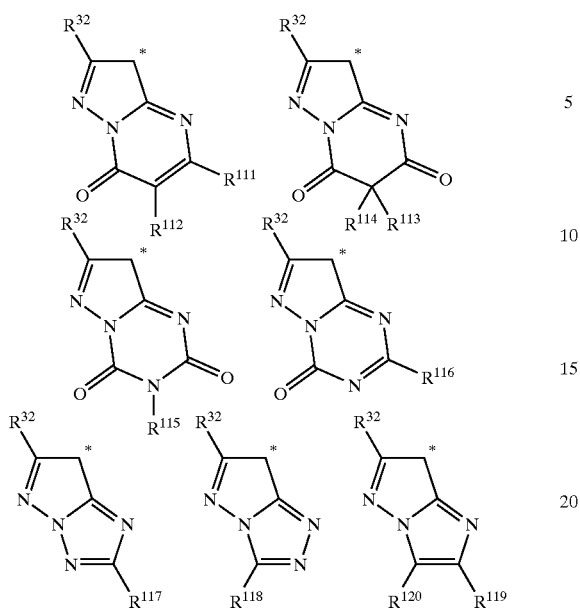

wherein, $R^{111}$ to $R^{120}$ have the same meanings as described above.

In formula (Cp-9), $Z^3$ preferably represents —C($R^{36}$)=, and preferred are the case where $R^{36}$ is a hydrogen atom or an acylamino group, $R^{33}$ and $R^{34}$ each represents a hydrogen atom, a halogen atom, an alkyl group or acylamino group, and $R^{35}$ represents a hydrogen atom or an alkyl group, and the case where $R^{34}$ and $R^{36}$ are coupled together to form a benzene ring which may be substituted with a halogen atom or an amino, alkylamino, arylamino, heterocyclic amino, acylamino, ureido, alkoxycarbonylamino, alkylsulfonylamino or arylsulfonylamino group.

In formula (Cp-10), preferred as $R^{37}$ and $R^{38}$ are a cyano group and alkoxycarbonyl groups, preferred as $R^{39}$ are a hydrogen atom, halogen atoms, alkyl groups, aryl groups, alkoxy groups, aryloxy groups, an amino group, alkylamino groups, arylamino groups, heterocyclic amino groups, acylamino groups, ureido groups, alkoxycarbonylamino groups, alkylsulfonylamino groups, arylsulfonylamino groups, alkylthio groups and arylthio groups, preferred as u is an integer of from 0 to 2, and preferred as $Z^4$ is —SO$_2$—.

In formula (Cp-11), preferred as $R^{40}$ and $R^{41}$ are a cyano group and alkoxycarbonyl groups, preferred as $R^{42}$, $R^{43}$ and $R^{44}$ are a hydrogen atom, halogen atoms, alkyl groups, aryl groups, alkoxy groups, aryloxy groups, an amino group, acylamino groups, ureido groups, alkoxycarbonylamino groups, alkylsulfonylamino groups, arylsulfonylamino groups, alkylthio groups and arylthio groups.

Among the dissociative direct dyes (1), those having as A the group of formula (Cp-1), (Cp-2), (Cp-3), (Cp-4) or (Cp-8) are more preferred.

Preferable specific examples of the dissociative direct dye (1) will next be shown.

D-1

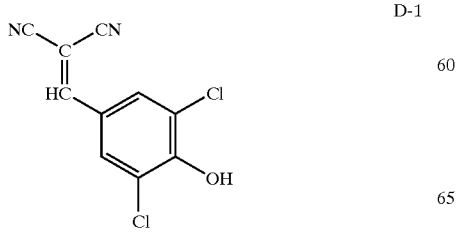

D-2

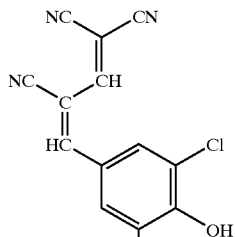

D-3

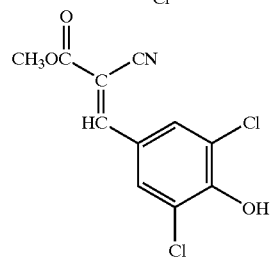

D-4

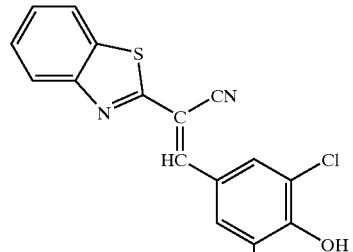

D-5

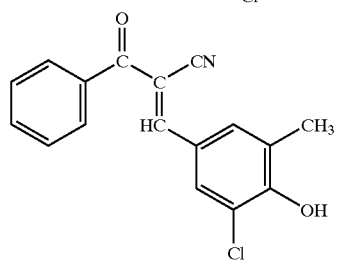

D-6

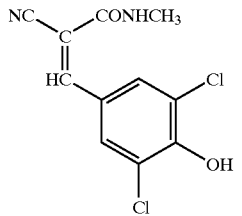

D-7

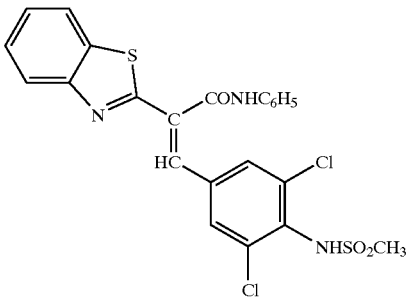

D-8
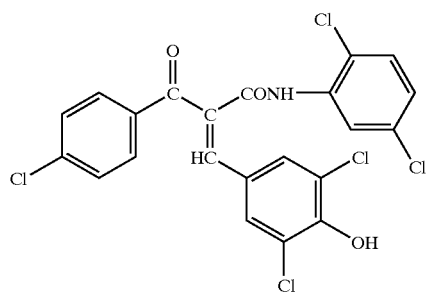
D-9
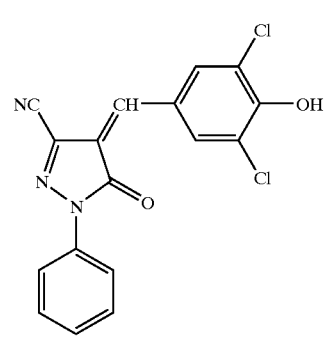
D-10
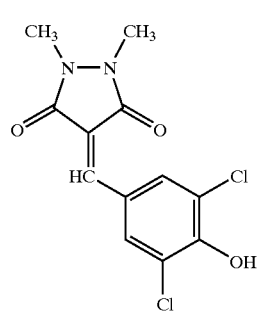
D-11
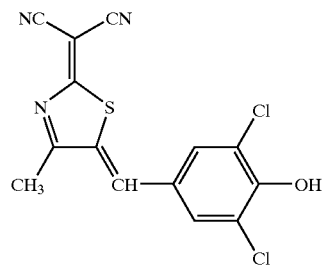
D-12
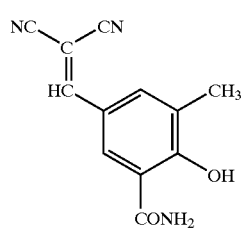
D-13
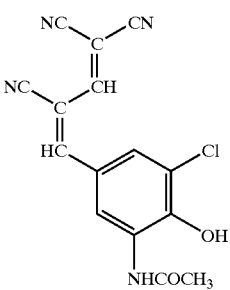
D-14
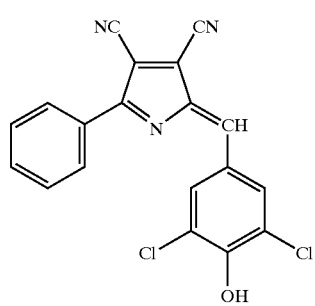
D-15
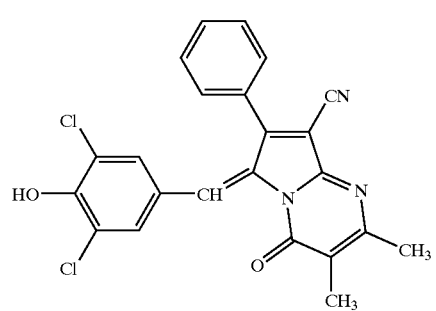
D-16
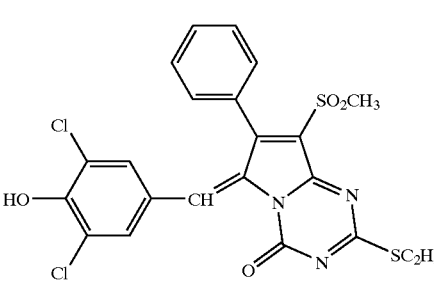
D-17
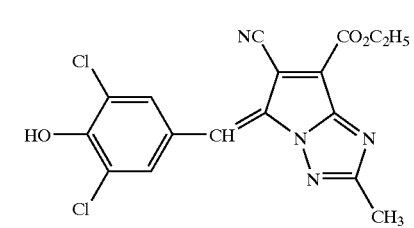

-continued

-continued
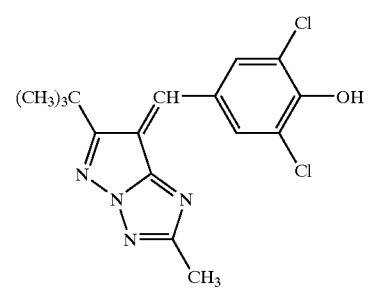
D-29
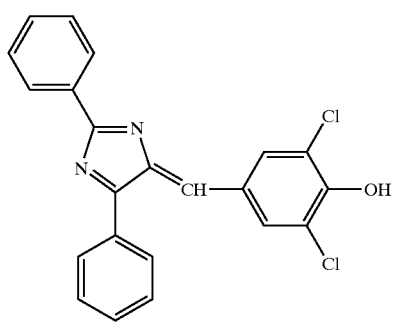
D-30
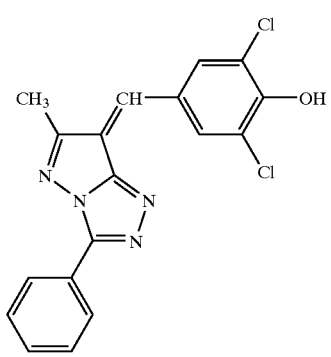
D-31
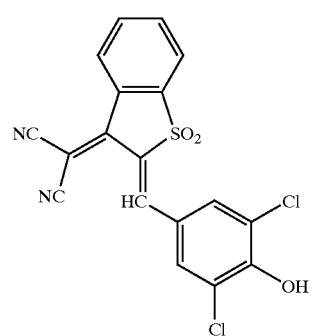
D-32
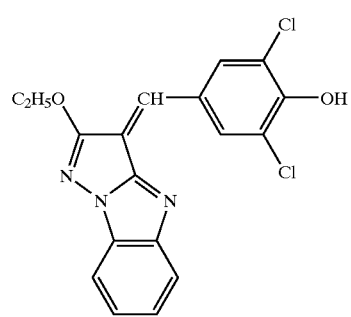
D-33
-continued
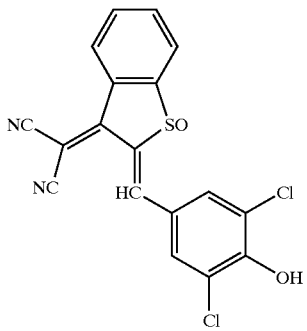
D-34
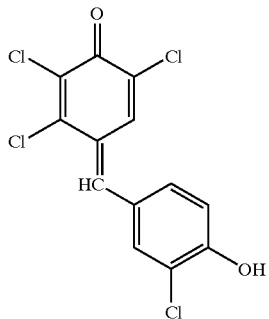
D-35
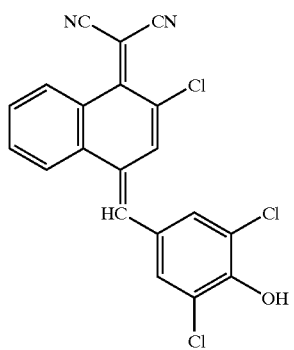
D-36
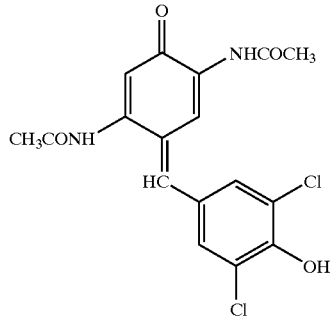
D-37
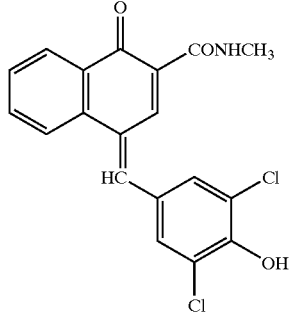
D-38

D-39
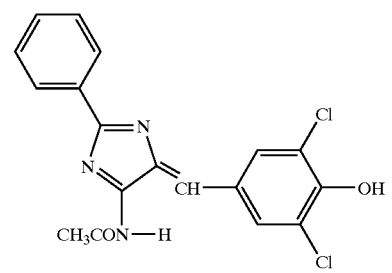
D-40
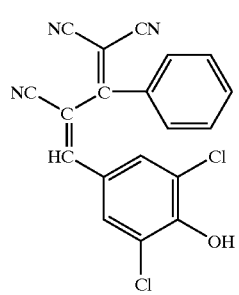
D-41
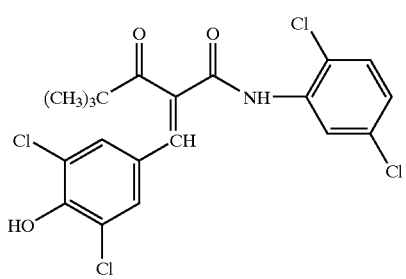
D-42
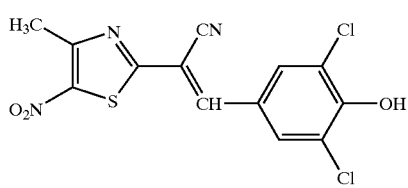
D-43
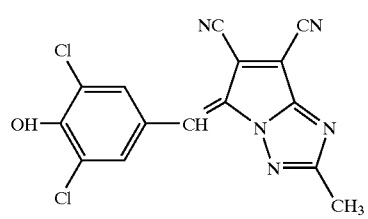
D-44
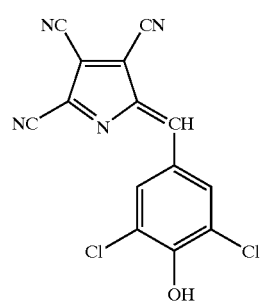
D-45
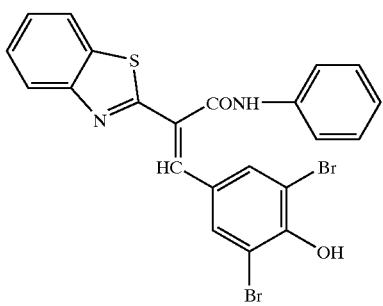
D-46
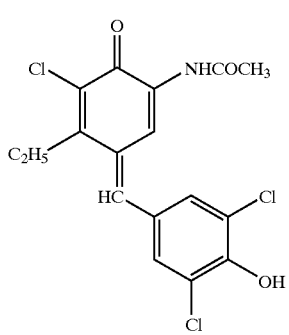
D-47
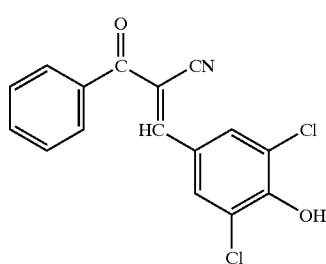
D-48
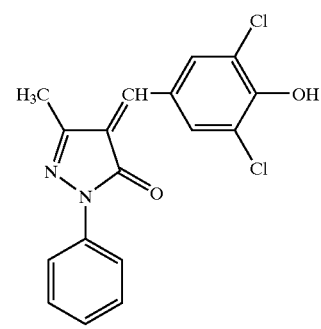
D-48
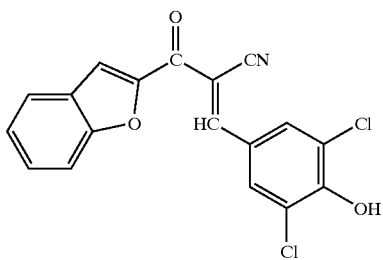

-continued

D-49

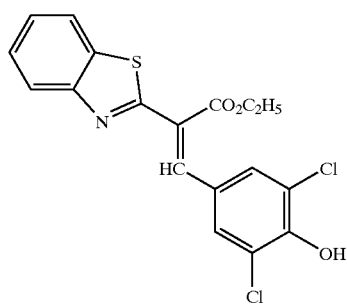

D-50

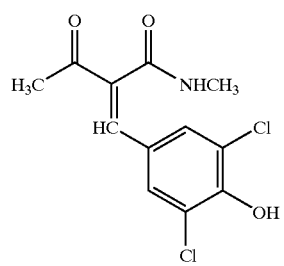

D-51

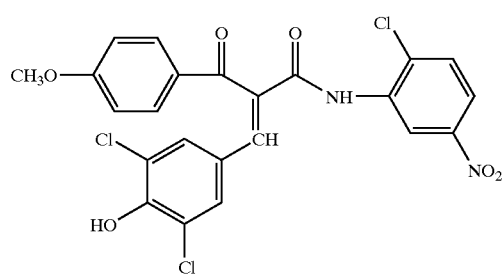

The dissociative direct dye (1) may be a salt of an organic or inorganic acid, or a salt of an organic or inorganic alkali. Examples of the organic or inorganic acid include hydrochloric acid, sulfuric acid, phosphoric acid, acetic acid, propionic acid, lactic acid and citric acid, while those of the organic or inorganic alkali include ammonium hydroxide, 2-ethanolammonium hydroxide, sodium hydroxide and potassium hydroxide.

The dissociative direct dye (1) can be synthesized for instance, in accordance with the below-described reaction scheme. Specifically, Dye-1, which is a dissociative direct dye (1), is available by subjecting Int-1, a so-called four-equivalent coupler having a hydrogen atom at a coupling active position, and Int-2 which is a benzaldehyde derivative to dehydration condensation in the presence of an appropriate catalyst and/or dehydrating agent. In the below-described scheme, V—C—W corresponds to A in formula (1).

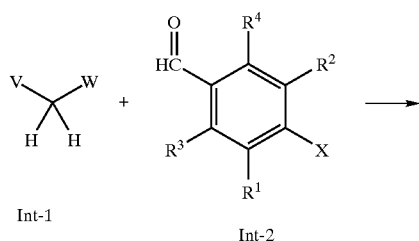

-continued

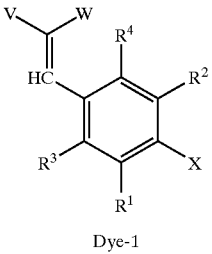

Dye-1

The four-equivalent coupler such as Int-1 can be synthesized in accordance with the process in the literature described above on a coupler in the field of silver halide color photosensitive materials. The benzaldehyde derivative such as Int-2 can be synthesized, for example, in accordance with the process as described on page 11 of Japanese Patent Laid-Open No. 48050/1994. The Exemplified Compound D-1 can be synthesized in accordance with the process as described on page 11 of Japanese Patent Laid-Open No. 48050/1994.

The pKa of the dissociative direct dye (1) is preferably from 1.5 to 9, especially preferably from 2 to 8, most preferably from 2 to 7.5 from the viewpoint of hair coloring performance and color retention attained by the dye. The pKa value can be determined in the following manner. First, a sample is dissolved in a 1:1 (volume ratio) solution of DMF and water to give its final concentration of $2 \times 10^{-5}$ mol/L. After adjustment of the pH of the resulting solution to 2 with 1.0 mol/L hydrochloric acid, the solution was titrated with a 1.0 mol/L aqueous solution of sodium hydroxide. Variations in a visible ultraviolet absorption spectrum are recorded and an inflection point is determined by regression analysis.

In the hair dye composition of the present invention, the dissociative direct dye (1) can be used in combination with another direct dye or an oxidation dye.

Examples of another direct dye include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 46 (C.I. 110825), Basic Red 76 (C.I. 12245), Basic Red 118 (C.I. 12251:1), Basic Yellow 28 (C.I. 48054) and Basic Yellow 57 (C.I. 12719); cationic dyes as described in Japanese Patent Laid-Open Nos. 2204/1983 and 118832/1997, and Japanese Language Laid-Open Publications (PCT) Nos. 501322/1996 and 507545/1996; and methine type cationic dyes having a cyanine structure represented by the following formulas:

yellow dye

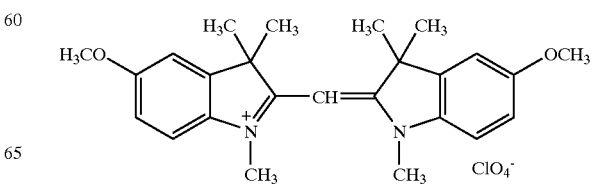

Orange dye

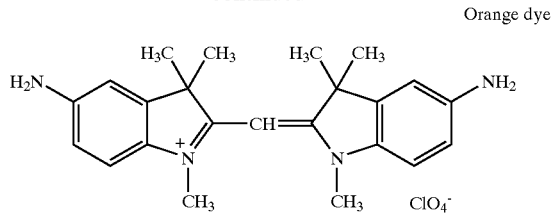

The dissociative direct dye (1) is added preferably in an amount of 0.0001 to 20 wt. %, more preferably 0.001 to 20 wt. %, more preferably from 0.05 to 10 wt. %, especially preferably from 0.1 to 5 wt. % based on the whole composition (after mixing of all the component parts when the composition is a two part or three part composition; this will be applied equally hereinafter). When another direct dye is used in combination, the total content of the dissociative direct dye (1) and another direct dye preferably ranges from 0.001 to 20 wt. %, more preferably from 0.01 to 20 wt. %, still more preferably from 0.05 to 10 wt. %, especially preferably from 0.1 to 5 wt. %.

In the hair dye composition of the present invention, the dissociative direct dye (1) exhibits a high storage stability within a wide pH range from 2 to 11 which is a pH range ordinarily employed for hair dyes, so that the hair dye composition of the present invention can be used at any pH in the above-described pH range. Use in a pH range of from 5 or greater is however preferred from the viewpoint of dyeing property. Moreover, owing to the high stability of the dissociative direct dye (1) against an alkali agent, the hair dye composition of the present invention can be used at a pH 8 or greater, particularly 8 to 11, which permits the composition to exhibit a high dyeing property, so that even after long-term storage, the high dyeing property can be kept without causing decomposition of the direct dye.

Examples of the alkali agent used for the hair dye composition of the present invention include ammonia, alkanolamines such as monoethanolamine and isopropanolamine or salts thereof, guanidium salts such as guanidine carbonate and hydroxides such as sodium hydroxide. The alkali agent is added preferably in an amount of from 0.01 to 20 wt. %, more preferably from 0.1 to 10 wt. %, especially preferably from 0.5 to 5 wt. % based on the whole composition.

Since the dissociative direct dye (1) has a high stability against an oxidizing agent, it can be applied to the hair after mixing with an oxidizing agent. In other words, it can be provided as a two-part composition composed of a first part containing the dissociative direct dye (1) and a second part containing an oxidizing agent. In this case, hair dyeing and bleaching can be carried out simultaneously, which facilitates more vivid hair dyeing.

Examples of the oxidizing agent include hydrogen peroxide, persulfates such as ammonium persulfate, potassium persulfate and sodium persulfate, perborates such as sodium perborate, percarbonates such as sodium percarbonate and bromates such as sodium bromate and potassium bromate. Hydrogen peroxide is especially preferred from the viewpoints of hair bleaching property, stability and effectiveness of the dissociative direct dye (1). Hydrogen peroxide may be used in combination with another oxidizing agent. The oxidizing agent is added preferably in an amount of from 0.5 to 10 wt. %, especially preferably from 1 to 8 wt. %, based on the whole composition.

The first part containing the dissociative direct dye (1) and the second part containing the oxidizing agent are mixed at a volume ratio preferably ranging from 2:1 to 1:3.

In the hair dye composition of the present invention, an oxidation dye can be used in combination with the dissociative direct dye (1). Such combined use enables considerably vivid and intense dyeing which cannot be accomplished by the single use of the oxidation dye. For the oxidation dye, known developers and couplers ordinarily employed for an oxidation type hair dye can be used.

Examples of the developer include paraphenylenediamine, toluene-2,5-diamine, 2-chloroparaphenylenediamine, N-methoxyethyl-paraphenylenediamine, N,N-bis(2-hydroxyethyl)-paraphenylenediamine, 2-(2-hydroxyethyl)-paraphenylenediamine, 2,6-dimethyl-para-phenylenediamine, 4,4'-diaminodiphenylamine, 1,3-bis(N-(2-hydroxyethyl)-N-(4-aminophenyl)amino)-2-propanol, PEG-3,2,2'-paraphenylenediamine, paraminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraminopyrimidine, 2,5,6-triamino-4-hydroxypyrimidine and 4,5-diamino-1-(4'-chlorobenzyl)pyrazole and salts thereof.

Examples of the coupler include metaphenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, metaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, and 2,6-diaminopyridine and salts thereof.

As each of the developer and coupler, at least two of the above-described developers or couplers are usable. The content of each of them is preferably from 0.01 to 20 wt. %, especially preferably from 0.5 to 10 wt. % based on the whole composition.

To the hair dye composition of the present invention, an autoxidation dye typified by an indole or an indoline, or a known direct dye such as a nitro dye or a disperse dye can also be added.

Addition of a polyol, polyol alkyl ether, cationic or amphoteric polymer and/or silicone to the hair dye composition of the present invention is preferred, because the resulting composition can dye the hair uniformly and provides improved cosmetic effects of the hair.

In addition to the above-described components, those ordinarily employed as a raw material for cosmetics can be added to the hair dye composition of the present invention.

Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, anionic surfactants, protein derivatives, amino acids, antiseptics, chelating agents, stabilizers, antioxidants, plant extracts, crude drug extracts, vitamins, colorants, perfumes and ultraviolet absorbers.

The hair dye composition of the present invention can be prepared in a conventional manner to form a one-part composition, a two-part composition having a first part containing an alkali agent and a second part containing an oxidizing agent, or a three-part composition having, in addition to these two parts, a powdery oxidizing agent such as persulfate. The direct dye (1) may be incorporated in at least one of these parts of the two-part or three-part composition. When the hair dye composition of the present invention is one-part type, it is applied to the hair directly, while when it is two- or three-part type, these parts are mixed just before hair dyeing and the mixture is applied to the hair.

In the case of preparation of a two-part type hair dye composition, the first part is typically prepared by mixing the dissociative direct dye (1) and optionally an oxidation dye and adjusting the pH of the mixture to 8 to 12 with an alkali agent such as ammonia. The second part is prepared by incorporating about 2 to 6 wt. % of hydrogen peroxide, adjusting the mixture to weakly acidic with phosphoric acid. When the composition is a three-part type, a persulfate is mixed with an inert substance such as talc or dextrin and a bonding agent to convert the mixture into a granular substance containing about 5 to 95 wt. % of persulfate. The granular substance is added to a mixture of the first part and the second part upon use.

The hair dye composition of the present invention can be provided in the form of powder, transparent liquid, emulsion, cream, gel, paste, aerosol, aerosol foam or the like. It preferably has a viscosity of 2000 to 100000 mPa·s upon its application to the hair (after mixing of all the parts when the composition is a two-part or three-part type). The above-described viscosity is measured at 20° C. by using a Brookfield rotary viscometer (No. 5 spindle, 5 rpm).

EXAMPLES

The synthesis examples of the dissociative direct dye (1) will next be described specifically.

Synthesis Example 1

Synthesis of Exemplified Compound D-4

Synthesis was conducted in accordance with the following scheme.

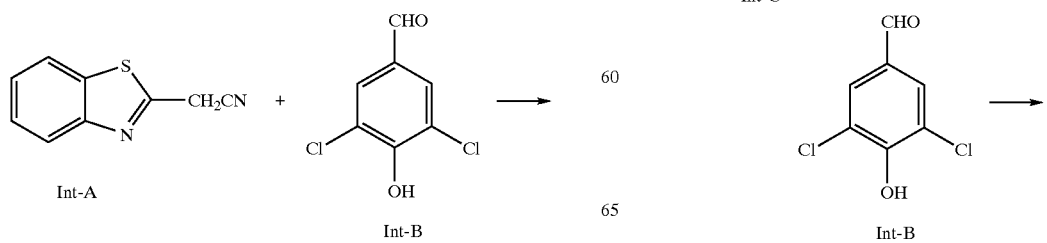

-continued

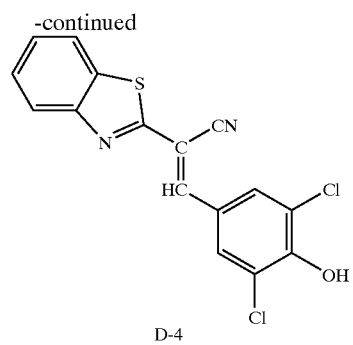

D-4

To 100 mL of toluene were added 3.5 g of benzothiazolylacetonitrile (Int-A), 3.8 g of 3,5-dichloro-4-hydroxybenzaldehyde (Int-B), and 0.6 g of ammonium acetate. The resulting mixture was heated under reflux for 1.5 hours while dehydrating using a Dean Stark water separator. After addition of 30 mL of ethyl acetate and stirring, the crystals thus precipitated were collected by filtration. The resulting crystals were added to 100 mL of water containing 1.0 mL of concentrated hydrochloric acid, followed by stirring at room temperature for 30 minutes. The crystals were collected by filtration and washed while pouring thereon 50 mL of water and then 30 mL of acetonitrile. The crystals thus obtained were air dried, whereby 2.6 g of Exemplified Compound D-4 was obtained as yellowish brown crystals (yield: 39%).

Synthesis Example 2

Synthesis of Exemplified Compound D-27

Synthesis was conducted in accordance with the following scheme.

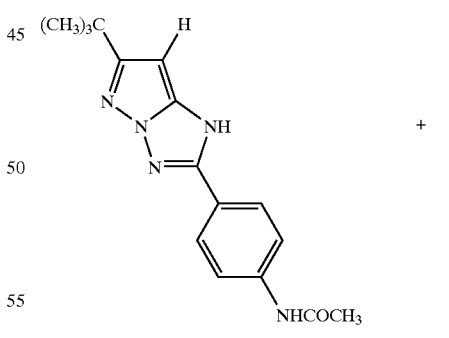

Int-C

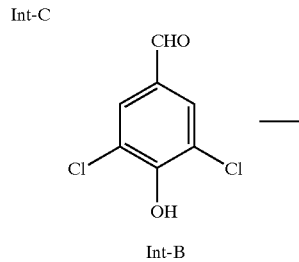

Int-B

-continued

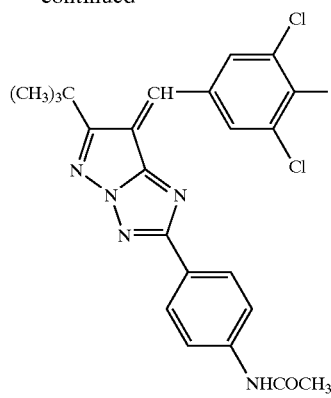

D-27

To 100 mL of toluene were added 1.5 g of Int-C, 1.1 g of 3,5-dichloro-4-hydroxybenzaldehyde (Int-B), 10 mL of N,N-dimethylacetamide and 0.1 g of ammonium acetate. The resulting mixture was heated under reflux for 10 hours while dehydrating using a Dean Stark water separator. After cooling to room temperature, the crystals thus precipitated were collected by filtration and washed while pouring thereon 20 mL of acetonitrile. The crystals thus obtained were added to 50 mL of water containing 0.5 mL of concentrated hydrochloric acid, followed by stirring at room temperature for 30 minutes. The crystals were collected by filtration, washed while pouring thereon 30 mL of water and then air dried, whereby 2.16 g of Exemplified Compound D-27 was obtained as yellowish orange crystals (yield: 92%).

Synthesis Example 3

Synthesis of Exemplified Compound D-29

Synthesis was conducted in accordance with the following scheme:

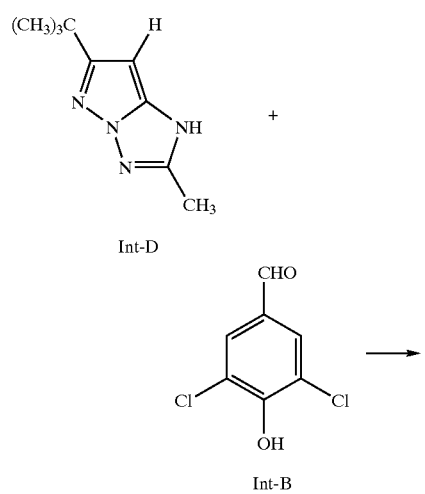

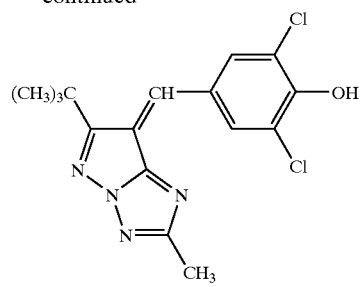

D-29

To 50 mL of toluene were added 1.8 g of Int-D, 1.9 g of 3,5-dichloro-4-hydroxybenzaldehyde (Int-B), 10 mL of N,N-dimethylacetamide and 0.1 g of ammonium acetate. The resulting mixture was heated under reflux for 2 hours while dehydrating using a Dean Stark water separator. After cooling to room temperature, the crystals thus precipitated were collected by filtration and washed while pouring thereon 20 mL of acetonitrile. The crystals thus obtained were added to 50 mL of water containing 0.5 mL of concentrated hydrochloric acid, followed by stirring at room temperature for 30 minutes. The crystals were collected by filtration, washed while pouring thereon 30 mL of water, 10 mL of acetonitrile and 10 mL of ethyl acetate successively and then air dried, whereby 2.21 g of Exemplified Compound D-29 was obtained as yellow crystals (yield: 62%).

Examples 1 to 3

Hair dye foams as shown in Table 1 were prepared in a manner known per se in the art.

TABLE 1

|  | Examples | | |
|---|---|---|---|
| Component (wt. %) | 1 | 2 | 3 |
| Dye (D-4) | 0.5 | — | — |
| Dye (D-27) | — | 0.5 | — |
| Dye (D-29) | — | — | 0.5 |
| Monoethanolamine | 1 | 1 | 1 |
| Ethanol | 15 | 15 | 15 |
| Propylene glycol | 10 | 10 | 10 |
| Polyoxyethylene (20) octyldodecyl ether | 10 | 10 | 10 |
| | 3 | 3 | 3 |
| Polyoxyethylene (9) tridecyl ether | 6 | 6 | 6 |
| Polyoxyethylene (3) tridecyl ether | 8 | 8 | 8 |
| Oleic diethanolamide | 2 | 2 | 2 |
| Oleyl alcohol | q.s. *1 | q.s. *1 | q.s. *1 |
| Ammonium chloride | 10 | 11 | 12 |
| LPG (4.0 kg/cm$^2$) | Balance | Balance | Balance |
| Purified water | | | |

*1: an amount to adjust the pH to 8.5

The above-described hair dye foams were each applied to the goat hair at 30° C. and was caused to act on the hair for 20 minutes. The hair thus dyed was then washed with an ordinarily used shampoo, followed by drying. As a result of the observation of the color tone of the dyed hair, it exhibited good dyeing property and resistance to shampoo.

Examples 4 to 7

Two-part hair dyes as shown in Table 2 were prepared in a manner known per se in the art.

TABLE 2

| Component (wt. %) | Examples | | | |
|---|---|---|---|---|
| | 4 | 5 | 6 | 7 |
| 1-st part | | | | |
| Dye (D-4) | 0.5 | — | — | — |
| Dye (D-27) | — | 0.5 | 0.5 | — |
| Dye (D-29) | — | — | — | 0.5 |
| HC Red 3 | — | 0.2 | — | — |
| p-Aminophenol | — | — | 0.2 | 0.2 |
| p-Amino-o-cresol | — | — | 0.2 | 0.2 |
| Ammonia (28 wt. %) | 6 | 6 | 6 | 6 |
| Ethanol | 15 | 15 | — | — |
| Propylene glycol | 10 | 10 | 2 | 2 |
| Polyoxyethylene (20) octyldodecyl ether | 10 | 10 | — | — |
| Polyoxyethylene (40) cetyl ether | — | — | 2 | 2 |
| Polyoxyethylene (2) cetyl ether | 8 | 8 | 2.5 | 2.5 |
| Oleic diethanolamide | 2 | 2 | — | — |
| Oleyl alcohol | — | — | 1.5 | 1.5 |
| Stearyltrimethylammonium chloride | — | — | 1 | 1 |
| Cetanol | q.s. *2 | q.s *2 | 0.5 | 0.5 |
| Liquid paraffin | — | — | q.s. *2 | q.s. *2 |
| Ammonium chloride | 0.1 | 0.1 | 0.5 | 0.5 |
| Sodium sulfite | Balance | Balance | 0.1 | 0.1 |
| Tetrasodium edetate | | | Balance | Balance |
| Purified water | | | | |
| 2-nd part | | | | |
| Hydrogen peroxide | 6 | 6 | 6 | 6 |
| Methyl paraben | 0.1 | 0.1 | 0.1 | 0.1 |
| Phosphoric acid | q.s. *3 | q.s. *3 | q.s. *3 | q.s. *3 |
| Purified water | Balance | Balance | Balance | Balance |

*2: an amount to adjust the pH to 9.8.
*3: an amount to adjust the pH to 3.5

After 1 part by weight of the first part was mixed with 1 part by weight of the second part, the resulting mixture was applied to the goat hair at 30° C. and was caused to act on the hair for 20 minutes. The hair thus dyed was then washed with an ordinarily used shampoo, followed by drying. As a result of the observation of the color tone of the dyed hair, it exhibited good dyeing property and resistance to shampoo.

What is claimed is:

1. A hair dye composition comprising a dissociative direct dye represented by the following formula (1):

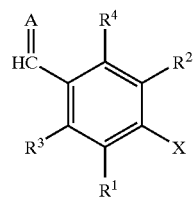

(1)

wherein, $R^1$, $R^2$, $R^3$ and $R^4$ each independently represents a hydrogen atom or a substituent, and X represents a hydroxyl group or —$NHSO_2R^5$, in which $R^5$ represents an alkyl, aryl or heterocyclic group, with the proviso that each of the groups may have one or more substituents; and in the dissociative direct dye (1) is a group represented by any one of the following formulas (Cp-4) through (Cp-11):

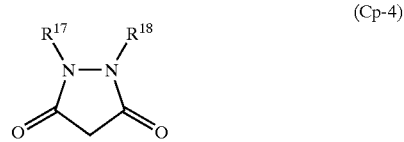

(Cp-4)

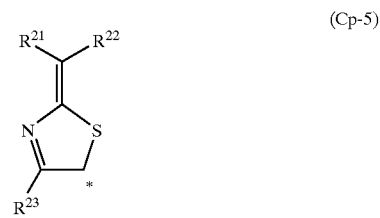

(Cp-5)

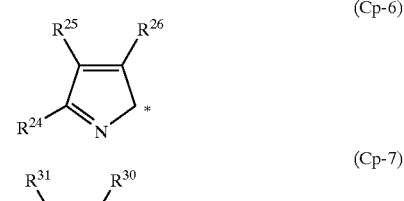

(Cp-6)

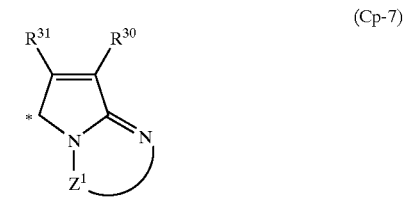

(Cp-7)

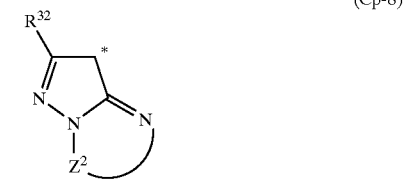

(Cp-8)

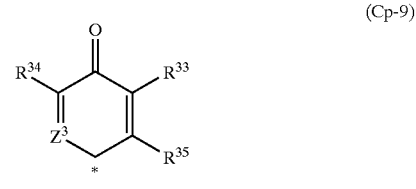

(Cp-9)

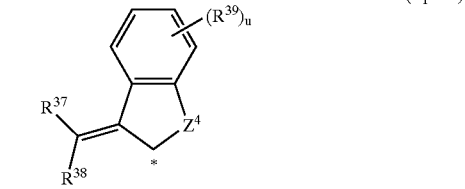

(Cp-10)

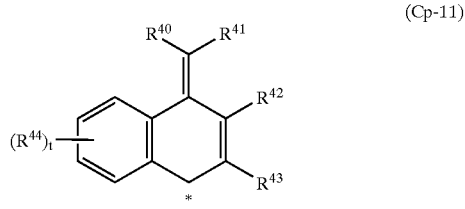

(Cp-11)

in formulas and (Cp-4) through (Cp-11), * is a position bonding to the benzylidene group in formula (1), in formula (Cp-4), $R^{17}$ and $R^{18}$ each independently represents a hydrogen atom or an alkyl, aryl or heterocyclic group, in formula (Cp-5), $R^{21}$ and $R^{22}$ each independently represents a cyano, carbamoyl, alkoxycarbonyl, alkylsulfonyl or arylsulfonyl group, and $R^{23}$ represents a hydrogen atom or an alkyl, aryl or heterocyclic group, in formula (Cp-6), $R^{24}$, $R^{25}$ and $R^{26}$ each independently represents a hydrogen atom or a substituent, in formula (Cp-7), $R^{30}$ and $R^{31}$ each independently represents a hydrogen atom or a substituent, and $Z^1$ represents an atomic group necessary for the formation of a 5- or 6-membered ring together with N—C=N, in formula (Cp-8), $R^{32}$ represents a hydrogen atom or a substituent, and $Z^2$ represents an atomic group necessary for the formation of a 5- or 6-membered ring together with N—C=N, in formula (Cp-9), $R^{33}$, $R^{34}$ and $R^{35}$ each independently represents a hydrogen atom or a substituent, $Z^3$ represents a nitrogen atom or —C($R^{36}$)=, $R^{36}$ representing a hydrogen atom or a substituent, with the proviso that when $Z^3$ represents —C($R^{36}$)=, $R^{34}$ and $R^{36}$ may be coupled to form a 5-membered or 6-membered ring, in formula (Cp-10), $R^{37}$ and $R^{38}$ each independently represents a cyano, carbamoyl, alkoxycarbonyl, alkylsulfonyl or arylsulfonyl group, $R^{39}$ represents a hydrogen atom or a substituent, u stands for an integer of from 0 to 4, and $Z^4$ represents —SO$_2$— or —SO—, and in formula (Cp-11), $R^{40}$ and $R^{41}$ each independently represents a cyano, carbamoyl, alkoxycarbonyl, alkylsulfonyl or arylsulfonyl group, $R^{42}$, $R^{43}$ and $R^{44}$ each independently represents a hydrogen atom or a substituent, and t stands for an integer of from 0 to 4, with the proviso that the above-described groups may have one or more substituents).

2. A hair dye composition of claim 1, wherein $R^1$ and $R^2$ in the dissociative direct dye (1) are each a hydrogen or halogen atom, or an alkyl, cyano, acylamino, ureido, alkoxycarbonylamino, aryloxycarbonylamino, sulfamoylamino, alkylsulfonylamino, arylsulfonylamino, alkoxycarbonyl, sulfamoyl or carbamoyl group.

3. A hair dye composition of claim 1, wherein $R^3$ and $R^4$ in the dissociative direct dye (1) are each a hydrogen atom, a halogen atom, or an alkyl or acylamino group which may be substituted.

4. A hair dye composition of claim 1, wherein X in the dissociative direct dye (1) is a hydroxyl group or —NHSO$_2$R$^5$, in which $R^5$ is an alkyl group which may be substituted.

5. A hair dye composition of claim 1, wherein A in the dissociative direct dye (1) is a group (which may have one or more substituents) selected from the groups represented by:

formula (Cp-4) in which $R^{17}$ and $R^{18}$ are each an alkyl or aryl group, formula (Cp-5) in which $R^{21}$ and $R^{22}$ are each a cyano, carbamoyl or alkoxycarbonyl group, and $R^{23}$ is a hydrogen atom, alkyl group or alkyl group, formula (Cp-6) in which $R^{24}$ is a hydrogen atom or an aryl, acylamino, alkylsulfonylamino or arylsulfonylamino group, and $R^{25}$ and $R^{26}$ are each a hydrogen atom or an aryl, alkoxycarbonyl, carbamoyl, alkylsulfonyl, arylsulfonyl or cyano group, formula (Cp-7) in which $R^{30}$ and $R^{31}$ are each a hydrogen atom or an alkyl, aryl, heterocyclic, alkoxycarbonyl, carbamoyl, alkylsulfonyl, arylsulfonyl or cyano group, and $Z^1$ is a group capable of forming the following ring systems:

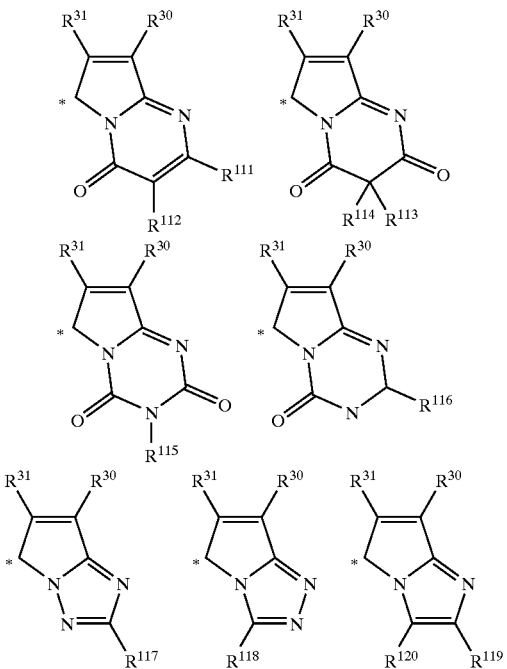

wherein, $R^{111}$ represents a hydrogen atom or an alkoxy, amino, alkylamino, arylamino, heterocyclic amino, acylamino, ureido, alkoxycarbonylamino, aryloxycarbonylamino, sulfamoylamino, alkylsulfonylamino, arylsulfonylamino, alkylthio, arylthio or heterocyclic thio group, $R^{112}$ represents a hydrogen or halogen atom, or an alkyl, acyl, carbamoyl or alkoxycarbonyl group, $R^{113}$ and $R^{114}$ each independently represents a hydrogen atom or an alkyl group, $R^{115}$ represents a hydrogen atom or an alkyl group, and $R^{116}$ represents a hydrogen atom or an alkyl, aryl, alkoxy, aryloxy, amino, alkylamino, arylamino, heterocyclic amino, acylamino, ureido, alkoxycarbonylamino, alkylsulfonylamino, arylsulfonylamino, alkylthio or arylthio group, $R^{117}$ and $R^{118}$ each independently represents a hydrogen atom or an alkyl, aryl or heterocyclic group, and $R^{119}$ and $R^{120}$ each independently represents a hydrogen atom or an alkyl, aryl, heterocyclic, acyl, alkoxycarbonyl or carbamoyl group or they may be coupled together to form a benzene ring, formula (Cp-8) in which $R^{32}$ is a hydrogen atom or an alkyl, aryl, heterocyclic, alkoxycarbonyl, carbamoyl, alkylsulfonyl, arylsulfonyl or cyano group, and $Z^2$ is a group capable of forming the following ring systems:

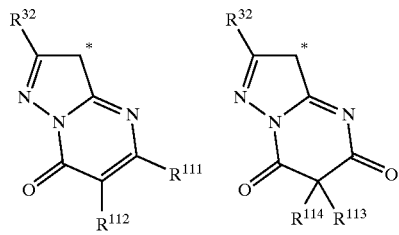

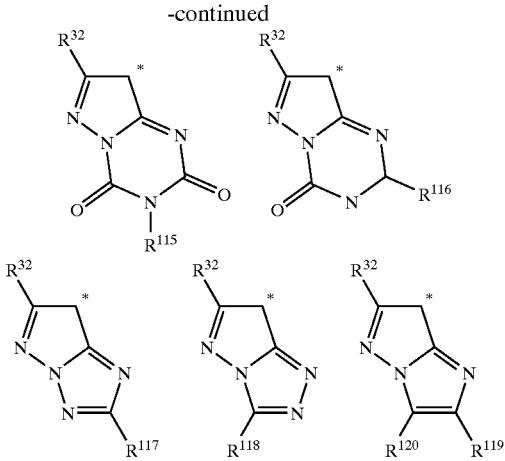

in which, $R^{111}$ to $R^{120}$ have the same meanings as described above, formula (Cp-9) in which $Z^3$ is —C($R^{36}$)═, $R^{36}$ represents a hydrogen atom or an acylamino group, $R^{33}$ and $R^{34}$ are each a hydrogen atom, a halogen atom, an alkyl group or acylamino group, and $R^{35}$ is a hydrogen atom or an alkyl group; or in which $Z^3$ is —C($R^{36}$)═, and $R^{34}$ and $R^{36}$ are coupled together to form a benzene ring which may be substituted with a halogen atom or an amino, alkylamino, arylamino, heterocyclic amino, acylamino, ureido, alkoxycarbonylamino, alkylsulfonylamino or arylsulfonylamino group, formula (Cp-10) in which $R^{37}$ and $R^{38}$ are a cyano or alkoxycarbonyl group, $R^{39}$ is a hydrogen or halogen atom or an alkyl, aryl, alkoxy, aryloxy, amino, alkylamino, arylamino, heterocyclic amino, acylamino, ureido, alkoxycarbonylamino, alkylsulfonylamino, arylsulfonylamino, alkylthio or arylthio group, u is an integer of from 0 to 2, and $Z^4$ is —SO$_2$—, and formula (Cp-11) in which $R^{40}$ and $R^{41}$ are each a cyano or alkoxycarbonyl group, and $R^{42}$, $R^{43}$ and $R^{44}$ are each a hydrogen or halogen atom or an alkyl, aryl, alkoxy, aryloxy, amino, acylamino, ureido, alkoxycarbonylamino, alkylsulfonylamino, arylsulfonylamino, alkylthio or arylthio group.

6. A hair dye composition of claim 1 or 5, wherein A in the dissociative direct dye (1) is a group represented by formula (Cp-4) or (Cp-8).

7. A hair dye composition comprising a dissociative direct dye represented by the following formula (1):

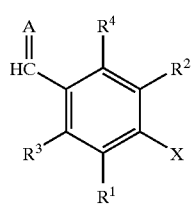

(1)

wherein, $R^1$, $R^2$, $R^3$ and $R^4$ each independently represents a hydrogen atom or a substituent, and X represents a hydroxyl group or —NHSO$_2$R$^5$, in which $R^5$ represents an alkyl, aryl or heterocyclic group, with the proviso that each of the groups may have one or more substituents; and A wherein A in the dissociative direct dye (1) is a group represented by the formula (Cp-3):

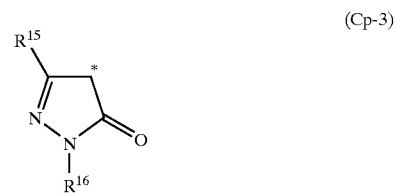

(Cp-3)

in formula (Cp-3), * is a position bonding to the benzylidene group in formula (1), in formula (Cp-3), $R^{15}$ represents a hydrogen atom or an alkyl, aryl, heterocyclic, amino, alkylamino, arylamino, heterocyclic amino, alkoxy, acylamino, alkoxycarbonylamino, ureido, alkoxycarbonyl, carbamoyl or cyano group, and $R^{16}$ represents a hydrogen atom or an alkyl or heterocyclic group.

8. A hair dye composition of claim 7, wherein $R^1$ and $R^2$ the dissociative direct dye (1) are each a hydrogen or halogen atom, or an alkyl, cyano, acylamino, ureido, alkoxycarbonylamino, aryloxycarbonylamino, sulfamoylamino, alkylsulfonylamino, arylsulfonylamino, alkoxycarbonyl, sulfamoyl or carbamoyl group.

9. A hair dye composition of claim 1, wherein $R^3$ and $R^4$ in the dissociative direct dye (1) are each a hydrogen atom, a halogen atom, or an alkyl or acylamino group which may be substituted.

10. A hair dye composition of claim 7, wherein X in the dissociative direct dye (1) is a hydroxyl group or —NHSO$_2$R$^5$, in which $R^5$ is an alkyl group which may be substituted.

11. A hair dye composition of claim 7, wherein A in the dissociative direct dye (1) is a group (which may have one or more substituents) selected from the groups represented by:

formula (Cp-3) in which $R^{15}$ is an alkyl, amino, alkylamino, arylamino, heterocyclic amino, alkoxy, acylamino, alkoxycarbonylamino, ureido, alkoxycarbonyl, carbamoyl or cyano group, and $R^{16}$ is a heterocyclic group.

12. A hair dye composition of claim 7, wherein A in the dissociative direct dye (1) is a group represented by formula (Cp-3).

* * * * *